(12) United States Patent
Caramella et al.

(10) Patent No.: US 8,633,169 B2
(45) Date of Patent: Jan. 21, 2014

(54) ANTIVIRAL TOPICAL FORMULATIONS IN THE FORM OF A BIO-ADHESIVE GEL

(75) Inventors: Carla Marcella Caramella, Abano Terme (IT); Silvia Rossi, Abano Terme (IT); Giuseppina Sandri, Abano Terme (IT); Giovanni Gennari, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 413 days.

(21) Appl. No.: 12/676,311

(22) PCT Filed: Sep. 3, 2008

(86) PCT No.: PCT/IB2008/002280
§ 371 (c)(1),
(2), (4) Date: Apr. 23, 2010

(87) PCT Pub. No.: WO2009/031006
PCT Pub. Date: Mar. 12, 2009

(65) Prior Publication Data
US 2010/0249156 A1 Sep. 30, 2010

(30) Foreign Application Priority Data
Sep. 5, 2007 (IT) .............................. MI2007A1724

(51) Int. Cl.
*A61K 31/715* (2006.01)

(52) U.S. Cl.
USPC ........... 514/54; 514/247; 514/359; 514/772.3

(58) Field of Classification Search
USPC ................... 514/54, 772.3, 247, 359
See application file for complete search history.

(56) References Cited

U.S. PATENT DOCUMENTS

| 5,585,379 | A | * | 12/1996 | Sintov et al. ............. 514/263.38 |
| 5,679,655 | A | * | 10/1997 | Gallina ........................... 514/54 |
| 2002/0015743 | A1 | | 2/2002 | Meybeck et al. |
| 2002/0151521 | A1 | | 10/2002 | Burke et al. |

FOREIGN PATENT DOCUMENTS

| EP | 10 23 899 A1 | 8/2000 |
| FR | 2767057 A1 | 2/1999 |

* cited by examiner

Primary Examiner — Shengjun Wang
Assistant Examiner — Shobha Kantamneni
(74) Attorney, Agent, or Firm — Birch, Stewart, Kolasch & Birch, LLP

(57) ABSTRACT

The invention relates to topical formulations in the form of a bioadhesive hydrophilic gel comprising acyclovir as active ingredient, Sodium hyaluronate and an acrylic polymer. Said formulations improve the local administration of acyclovir in the treatment of herpes infections, because they possess good properties of adherence to the mucosa and high resistance to physiological removal mechanisms.

7 Claims, 5 Drawing Sheets

ANTIVIRAL TOPICAL FORMULATIONS IN THE FORM OF A BIO-ADHESIVE GEL

FIELD OF INVENTION

The present invention relates to novel topical formulations of acyclovir in the form of a highly bioadhesive hydrophilic gel, containing low molecular weight hyaluronic acid in association with polyacrylic acid.

BACKGROUND TO THE INVENTION

Acyclovir is an acyclic analogue of the natural nucleoside 2'-deoxyguanosine which possesses antiviral activity against the Herpes virus, a DNA virus.

Mild genital and labial herpes infections cause the appearance of local blisters and ulcers of limited size, which may not require any pharmacological treatment, although the first-line treatment for mild herpes infections is local administration of 5% acyclovir.

Serious genital and labial herpes infections can give rise to extensive blistering and ulceration of the mucous membranes, sometimes accompanied by fever, lymphadenopathy and dysuria, and in some cases may also involve the cervix (Rawls, W. E. (1985). Herpes Simplex viruses. In "Virology" chapter 26, pp 527-561. Ed. Fields B. N., Knipe, D. M., Chanock, R. M., Melnick, J. L., Roizman, B., Raven Press, New York.). The preferred treatment for the said disorder in that case is oral administration of acyclovir (200 mg once a day), always associated with local treatment.

Acyclovir is administered locally in conventional dosage forms with a dosage pattern of five applications a day; however, this dose is unable to maintain therapeutically effective levels of the drug at the site of action for a long period. Local treatment often fails due to the active physiological removal mechanisms (physiological secretions and/or mechanical stress) which cause incorrect distribution of the drug in the mucocutaneous area affected by the infection, in view of the numerous applications required to maintain efficacious levels of the drug at the site of application.

To meet therapeutic requirements, formulations containing acyclovir which are intended for topical administration in areas affected by herpes lesions should consequently have good properties of adherence to the mucous membranes and high resistance to physiological removal mechanisms, so as to maintain close, protracted contact between the formulation and the mucosa or epidermis affected by the herpes lesions.

The mucoadhesive properties of semisolid drug delivery systems are due to the presence of semi-synthetic or natural polymers able to interact with the biological substrates. In contact with aqueous solvents, these polymers form hydrophilic gels characterised by a lattice in which water molecules are trapped.

Polyacrylic acids (PAA) are synthetic polymers widely used in local drug delivery systems. PAAs are characterised by good mucoadhesive properties and excellent thickening efficiency. Their crosslinked structure and substantial insolubility in water make PAAs suitable for use in controlled drug release systems (Singla A. K. et al., 2000, Drug Dev. Ind. Pharm. 29: 913-924).

Hyaluronic acid (HA) is a heteropolysaccharide composed of alternate residues of D-glucuronic acid and N-acetyl-D-glucosamine. It is a linear-chain polymer, with a molecular weight that can range between 50,000 and $13 \times 10^6$ Da, depending on the source from which it is obtained and the preparation methods used.

It is a glycosaminoglycan present in nature in the pericellular gels, the synovial fluid of the joints, the vitreous humour and the umbilical cord, and is widely distributed in the extracellular matrix of the connective tissues. HA is believed to perform regulatory and structural functions in the reconstruction of the tissues through modulation of fibroblast proliferation and the inflammatory response (Goa K. L. et al., 1994, Drugs, 47: 536-566).

HA therefore plays an important role in the biological organism and, together with those described above, also acts as mechanical support for the cells of many tissues such as skin, tendons, muscles and cartilage.

Mucoadhesive formulations containing synthetic polymers, including polyacrylic acids, and hyaluronic acid have already been disclosed as drug delivery systems in IT 1273742; however, the preferred polymer is Polycarbophil (polyacrylic acid crosslinked with divinyl glycol) in association with high molecular weight hyaluronic acid.

This invention relates to new topical formulations of acyclovir in the form of hydrophilic gels which are highly bioadhesive due to the presence of hyaluronic acid (with low molecular weight) or derivatives thereof, in association with polyacrylic acid for the treatment of all mucocutaneous lesions caused by Herpes Simplex or Herpes Zoster.

DESCRIPTION OF THE INVENTION

Figure 1:
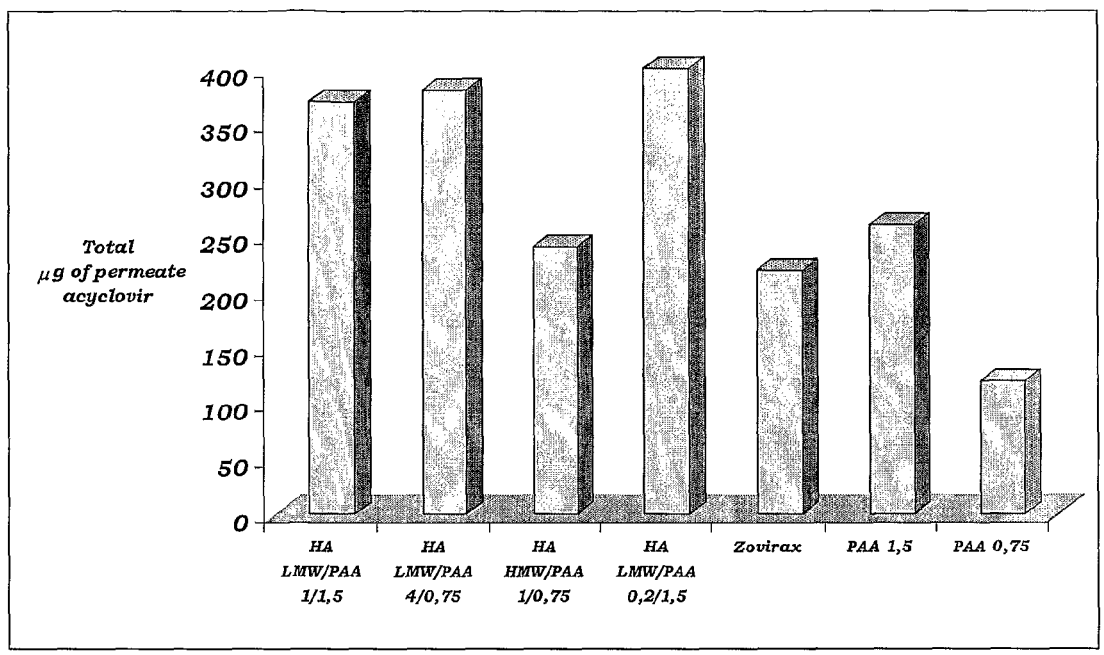
FIG. 1 presents permeation profiles of the acyclovir contained in formulations.

It has now been found that acyclovir can be advantageously formulated in the form of a hydrophilic gel with ideal viscoelastic and mucoadhesive properties, using vehicles containing salts of hyaluronic acid and/or derivatives thereof, in combination with at least one polyacrylic polymer called Carbopol® or Carbomer®.

The formulations of the invention are characterised by better release properties, better mucoadhesion properties, and lower leachability than known formulations available on the market. The viscosimetric properties of the gels according to the invention are also compatible with the manufacturing requirements (workability, packaging) and use requirements (extrusion, spreadability) of the product.

The HA derivatives which can be used in the novel formulations of the invention are listed below:

1. HA salified with organic and/or inorganic bases;
2. Hyaff®: esters of HA with alcohols in the aliphatic, arylaliphatic, cycloaliphatic, aromatic, cyclic and heterocyclic series, with a percentage of esterification which can vary, depending on the type and length of the alcohol used, from 0.1 to 100% (EP 216453 B1);
3. Hyadd®: amides of HA with amines of the aliphatic, arylaliphatic, cycloaliphatic, aromatic, cyclic and heterocyclic series, with an amidation percentage of 1 to 10%, preferably 4% (EP 1095064 B1);
4. O-sulphated derivatives of HA up to the 4th degree of sulphation (EP 0702699 B1);

5. ACP®: inner esters of HA with an internal esterification percentage ranging between 0.5 and 10%, and preferably 5% (EP 0341745 B1);

6. HA deacetylates: they derive from deacetylation of the N-acetyl-glucosamine fraction with a deacetylation percentage preferably between 0.1 and 30%, while all the carboxyl groups of HA can be salified with organic and/or inorganic bases (EP1313772 B1);

7. Hyoxx®: percarboxylated derivatives of HA obtained by oxidation of the primary hydroxyl of the N-acetyl-glucosamine fraction with a degree of percarboxylation of between 0.1 and 100%. All the carboxyl groups of HA can be salified with organic and/or inorganic bases (EP1339753).

The HA used in this invention, as such or in the preparation of its derivatives, may derive from any source, e.g. extraction from cockscombs (EP0138572 B1), fermentation (EP0716688 B1), or a technological process.

The salts of hyaluronic acid or derivatives thereof are preferably sodium salts of hyaluronic acid with a low molecular weight of between 80,000 and 300,000 Da, depending on the source and manufacturing technique. Hyaluronic acid with a molecular weight of between 90,000 and 230,000 Da is preferably used. The salt of hyaluronic acid or derivatives thereof is present in the formulations according to the invention in the percentage by weight of between 0.1 and 1%, preferably 0.2%.

The acrylic polymer is preferably Carbopol® 974P or Carbopol® 934P (also called Carbomer 974P and 934P respectively), available on the market from BF Goodrich, Ohio USA, and is present in the formulations according to the invention in the percentage by weight of between 1 and 5%, preferably 1.5%.

The percentage by weight of acyclovir can approx. range from 1 to 10%, and is preferably 5%. The formulations according to the invention contain conventional excipients compatible with the topical administration to the skin and mucous membranes. In addition to preservatives (such as parabens), the formulations can contain, for example, glycerol and propylene glycol as wetting agents, polyethylene glycol (such as PEG 400) as solubiliser of the active ingredient, and pH regulators such as triethanolamine.

The Applicant has surprisingly found that the therapeutic efficacy of the formulations of the invention is particularly advantageous due to the association between low molecular weight hyaluronic acid sodium salt and Carbopol® 974P or Carbopol® 934P, as it produces:

1. a significant increase in the mucoadhesive properties of the formulations of the invention compared with the well-known commercial formulation of acyclovir cream (Zovirax®);

2. a significant increase in the cumulative amount of drug that permeates into the mucosa compared with acyclovir cream;

3. a significant increase in the release of the active ingredient compared with acyclovir cream;

4. a significant reduction in the percentage of drug removed from the skin/mucosa by means of physiological removal mechanisms compared with acyclovir cream ("washability" test).

The tests conducted to prove this finding were performed with formulations based on low molecular weight HA sodium salt (mean molecular weight: 200 KD) and high molecular weight HA sodium salt (mean molecular weight: 1800 KD), in association with Carbopol for the release of the active ingredient acyclovir.

Gel Preparation

Hyaluronic acid sodium salt of fermentative origin with a low molecular weight (LMW-HA) of 90-230 KDa (mean molecular weight: 200 KDa), or HA sodium salt (HMW-HA) with a high molecular weight (mean molecular weight: 1800 KDa), or the sulphated derivative of HA or the benzyl ester of HA used for the formulations reported below (HA was not added for the control formulations), was hydrated in bidistilled sterile water, after hot solubilisation of the preservatives methyl p-hydroxybenzoate and propyl p-hydroxybenzoate. PEG 400 and Carbopol® 974P or 934P were added to the solution under magnetic stirring. After complete hydration of the Carbopol®, TEA (triethanolamine) was added to buffer the polymer solution to pH 6.0 so that the Carbopol® gelled. Glycerol, propylene glycol and finally acyclovir were then incorporated, still under stirring. The gel thus obtained was homogenised with an Ultraturrax turbine stirrer (T 25 Janke & Kunkel IKA®-Labortechnick, G) for 5 minutes at the speed of 13,500 rpm.

Formulation 1:

| Ingredient | Amount (% w/w) |
|---|---|
| Acyclovir | 5.000 |
| Excipients | |
| Carbopol ® 974P | 1.500 |
| Sodium hyaluronate (200 KDa) LMW-HA | 1.000 |
| Glycerol | 10.000 |
| Propylene glycol | 6.675 |
| Polyethylene glycol 400 (PEG 400) | 6.675 |
| Methyl-p-hydroxybenzoate | 0.080 |
| Propyl-p-hydroxybenzoate | 0.020 |
| Purified water | 69.05 |
| Triethanolamine | q.s. for pH 6 |

Formulation 2:

| Ingredient | Amount (% w/w) |
|---|---|
| Acyclovir | 5.000 |
| Excipients | |
| Carbopol ® 974P | 0.750 |
| Sodium hyaluronate (200 KD) LMW-HA | 4.000 |
| Glycerol | 10.000 |
| Propylene glycol | 6.675 |
| Polyethylene glycol 400 (PEG 400) | 6.675 |
| Methyl-p-hydroxybenzoate | 0.080 |
| Propyl-p-hydroxybenzoate | 0.020 |
| Purified water | 66.800 |
| Triethanolamine | q.s. for pH 6 |

Formulation 3:

| TIngredient | Amount (% w/w) |
|---|---|
| Acyclovir | 5.000 |
| Excipients | |
| Carbopol ® 974P | 0.750 |
| Sodium hyaluronate (1,800 KD) HMW-HA | 1.000 |
| Glycerol | 10.000 |
| Propylene glycol | 6.675 |
| Polyethylene glycol 400 (PEG 400) | 6.675 |
| Methyl-p-hydroxybenzoate | 0.080 |

-continued

| Ingredient | Amount (% w/w) |
|---|---|
| Propyl-p-hydroxybenzoate | 0.020 |
| Purified water | 70.300 |
| Triethanolamine | q.s. for pH 6 |

Formulation 4:

| Ingredient | Amount (% w/w) |
|---|---|
| Acyclovir | 5.000 |
| Excipients | |
| Carbopol ® 974P | 1.500 |
| Sodium hyaluronate (200 KD) LMW-HA | 0.200 |
| Glycerol | 10.000 |
| Propylene glycol | 6.675 |
| Triethanolamine | 1.325 |
| Polyethylene glycol 400 (PEG 400) | 6.675 |
| Methyl-p-hydroxybenzoate | 0.200 |
| Propyl-p-hydroxybenzoate | 0.020 |
| Purified water | 68.405 |

Control Formulation (for Formulations 1, 4):

| Ingredient | Amount (% w/w) |
|---|---|
| Acyclovir | 5.000 |
| Excipients | |
| Carbopol ® 974P | 1.500 |
| Glycerol | 10.000 |
| Propylene glycol | 6.675 |
| Polyethylene glycol 400 (PEG 400) | 6.675 |
| Methyl-p-hydroxybenzoate | 0.080 |
| Propyl-p-hydroxybenzoate | 0.020 |
| Purified water | 70.050 |
| Triethanolamine | q.s. for pH 6 |

Control Formulation (for Formulations 2-3):

| Ingredient | Amount (% w/w) |
|---|---|
| Acyclovir | 5.000 |
| Excipients | |
| Carbopol ® 974P | 0.750 |
| Glycerol | 10.000 |
| Propylene glycol | 6.675 |
| Polyethylene glycol 400 (PEG 400) | 6.675 |
| Methyl-p-hydroxybenzoate | 0.080 |
| Propyl-p-hydroxybenzoate | 0.020 |
| Purified water | 70.800 |
| Triethanolamine | q.s. for pH 6 |

Two further controls were also prepared for Formulation 4 by replacing:

1. Carbopol 974 P (1.5% w/w) with Polycarbophil (Noveon®AA-1) (1.5% w/w), and LMW-HA (0.2% w/w) with HMW-HA with a molecular weight of $1\times10^6$ Da (0.2% w/w), or 2. replacing Carbopol 974 P (1.5% w/w) with Polycarbophil (1% w/w) and LMW-HA (0.2% w/w) with HMW-HA with a molecular weight of $1\times10^6$ Da (0.15% w/w), and adding polyvinyl alcohol (MW 30000-70000) (Sigma-Aldrich) (1.5% w/w).

These two controls are designed to perform specific mucoadhesion tests by comparison with formulation 4 to demonstrate that the topical compositions according to the invention are more effective than those of the prior art.

Further formulations containing HA derivatives, described below, were also prepared:

Formulation Based on O-Sulphated HA Derivative

| Ingredient | Amount (% w/w) |
|---|---|
| Acyclovir | 5.000 |
| Excipients | |
| Carbopol ® 934P | 1.500 |
| O-sulphated HA derivative, grade 3 | 0.200 |
| Glycerol | 10.000 |
| Propylene glycol | 6.675 |
| Triethanolamine | 1.325 |
| Polyethylene glycol 400 (PEG 400) | 6.675 |
| Methyl-p-hydroxybenzoate | 0.200 |
| Propyl-p-hydroxybenzoate | 0.020 |
| Purified water | 68.405 |

Formulation Based on HA Benzyl Ester

| Ingredient | Amount (% w/w) |
|---|---|
| Acyclovir | 5.000 |
| Excipients | |
| Carbopol ® 974P | 1.500 |
| 50% esterified HA benzyl ester | 0.200 |
| Glycerol | 10.000 |
| Propylene glycol | 6.675 |
| Triethanolamine | 1.325 |
| Polyethylene glycol 400 (PEG 400) | 6.675 |
| Methyl-p-hydroxybenzoate | 0.200 |
| Propyl-p-hydroxybenzoate | 0.020 |
| Purified water | 68.405 |

Characterisation of the Formulations

Mucoadhesion Measurements

Mucoadhesion was measured with a tensile stress tester (Ferrari M. C. et al., 1996, Drug Dev. Ind. Pharm. 22: 1223-1230).

Porcine vaginal mucosa was used as biological substrate.

The equipment, assembled on a support with a horizontal base, consisted of a load cell with a linearity interval of 0-20 N and sensitivity of ±4 mN, integral with a mobile carriage and connected to a personal computer (IBM AT, IBM, I) via an amplifier.

A motor fitted with a speed transformer moves a screw which, as it advances, pushes the load cell forward: the movement imparted by the motor is thus transmitted to the mobile carriage through the load cell.

100 mg of each formulation was applied to a filter paper disc with a diameter of 16 mm (in the case of FIG. 2) or 30 mm (in the case of FIG. 5), which was glued to the mobile carriage. A second filter paper disc, of the same diameter, was fixed to the sample holder, and the porcine vaginal mucosa was glued to it with acrylic glue.

The mobile carriage was placed in contact with the sample holder, and a pre-load of 2500 mN was applied to it. After 3 minutes the pre-load was removed and the carriage moved at a speed of 4 mm/min, until the interface between film and mucosa had completely separated. The movement values and adherence force values obtained from the load cell were acquired and recorded by the computer. A force/movement curve was then constructed, from which the mucoadhesion work parameter was obtained, calculated by the trapezoid rule, as the area underlying the force/movement curve.

Permeation Test

A Franz diffusion cell with a 20 mm diameter opening was used for the permeation measurements. The permeation was measured with porcine vaginal mucosa preserved in isotonic phosphate buffer at pH 7.4 until the time of use. The whole mucosa was used, without thinning, so as not to damage the epithelium. 100 mg of each formulation was placed on a circular area of mucosa (diameter 25 mm), which was positioned on an absorbent paper disc to separate the donor compartment from the receptor compartment. An isotonic buffer at pH 7.4 was placed in the receptor compartment to thermostat the mucosa and keep it hydrated. The permeation test was conducted for 5.5 hours. At the end of the test, the tissue was frozen at −20° C. The tissue was then cut into slices 40 μm thick with a cryostat (Leica CM 1510, Leica Microsystems, I). The drug which had permeated the various layers of tissue was extracted according to the method described in Volpato N. M. et al., 1997, J Pharm. Biomed Anal, 16:515-520, and assayed by the HPLC method. The amount of drug in relation to the depth of the tissue, and the total amount of drug recovered from the mucosa, were evaluated. Six replications were performed for each sample.

"Washability" Test

The Franz diffusion cell had to be modified in order to perform the washability measurements. The donor compartment used for these measurements was equipped with two side arms to allow the entry and exit of the acetate buffer at pH 5.0, thermostated at 37° C., at a flow rate of 0.2 ml/min, to simulate the vaginal secretions. The donor compartment has an air vent at the tip, which is closed by a screw at the compartment-filling stage.

Porcine vaginal mucosa approx. 1 cm thick, stored at −20° C., was used as biological substrate. After thawing, the mucosa was laid on a dialysis membrane (cut-off 12-14 kD) and positioned in the donor compartment. 100 mg of each formulation was then placed on a 2 $cm^2$ area of mucosa. The receptor compartment containing isotonic phosphate buffer at pH 7.4 was used for the sole purpose of keeping the mucosa hydrated and thermostated at the temperature of 37° C. The backflow sample from the donor compartment was collected in a beaker fitted with a magnetic stirring system. 1 ml of backflow buffer was taken up from the beaker at pre-set times (30 minutes) for a total of 5.5 hours, and replaced with 1 ml of fresh buffer. The total amount of drug "washed away" was measured by spectrophotometry, as described in the release test.

Each sample was analysed in triplicate.

Release Test

The release test was performed with a Franz diffusion cell with a 20 mm diameter opening. The system, consisting of an upper donor compartment and a lower "receptor" compartment with a volume of 10 ml, was thermostated with an external jacket at the temperature of 37° C. Acetate buffer at pH 5.0 was used as receptor phase to imitate the vaginal environment. The buffer was degassed before use and stirred during the measurements at a constant speed with a magnetic anchor. The two compartments were separated by a dialysis membrane with a 12-14 kD cut-off. The dialysis membrane was boiled in distilled water for 10 minutes before use and then spread over the opening of the receptor compartment, taking care not to trap air during the operation.

100 mg of the formulations tested was applied to a filter paper disc with a constant area (2 $cm^2$), which was laid on the dialysis membrane wetted with the receptor phase to prevent air from being trapped between the two surfaces. The donor compartment was fixed to the receptor compartment with a clip. The upper opening of the donor compartment was closed by a waterproof membrane. At pre-set intervals, for a total of 5.5 hours, 500 μl of receptor phase was taken up with a microsyringe from the centre of the receptor compartment through the sampling arm.

The volume taken up was replaced with fresh solvent each time. The drug was assayed spectrophotometrically, after suitable dilution of the samples, at the wavelength of 252 nm.

Three replications were performed for each sample.

Results

Permeation Test

FIG. 1 shows the permeation profiles (in the different layers of the porcine vaginal mucosa) of the acyclovir contained in formulations 1-4 and in the commercial formulation Zovirax®, compared with the respective control formulations measured at the end of the test (5.5 hours). The amount of acyclovir assayed in the first layers relates to a thickness of 0-600 μm. Slices with a depth of up to 5 mm were analysed. The drug was found in the different layers examined in all cases. The amount of drug measured tends to decrease with distance from the surface of the mucosa. Formulation 4 produces a higher drug content in the tissue analysed than formulations 1 and 2, which present almost identical distributions. The commercial formulation, formulation 3 containing high molecular weight HA, and control formulation PAA 1.5, present almost identical profiles, much inferior to the other formulations 1, 2 and 4. Control formulation PAA 0.75 has the lowest distribution profile of all.

Mucoadhesion Measurements

Figure 2:
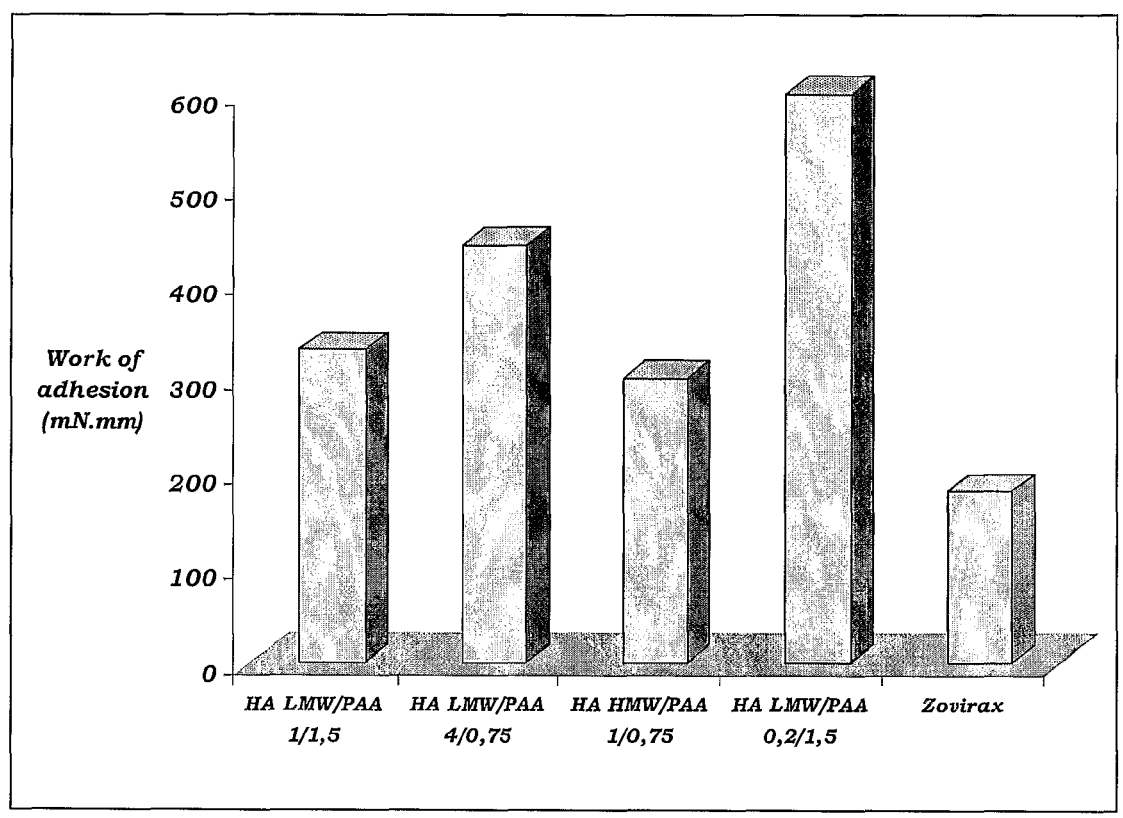
FIG. 2 presents mucoadhesion work values for formulations.

FIG. 2 shows the mucoadhesion work values of formulations 1-4 and the commercial formulation. As will be seen, all the formulations present significantly higher mucoadhesion values than the commercial formulation. In particular, formulation 4 presents a much higher value than all the others examined, indicating that the formulation containing low molecular weight HA at the concentration of 0.2%, in combination with 1.5% PAA, presents the best mucoadhesive properties.

Figure 5:
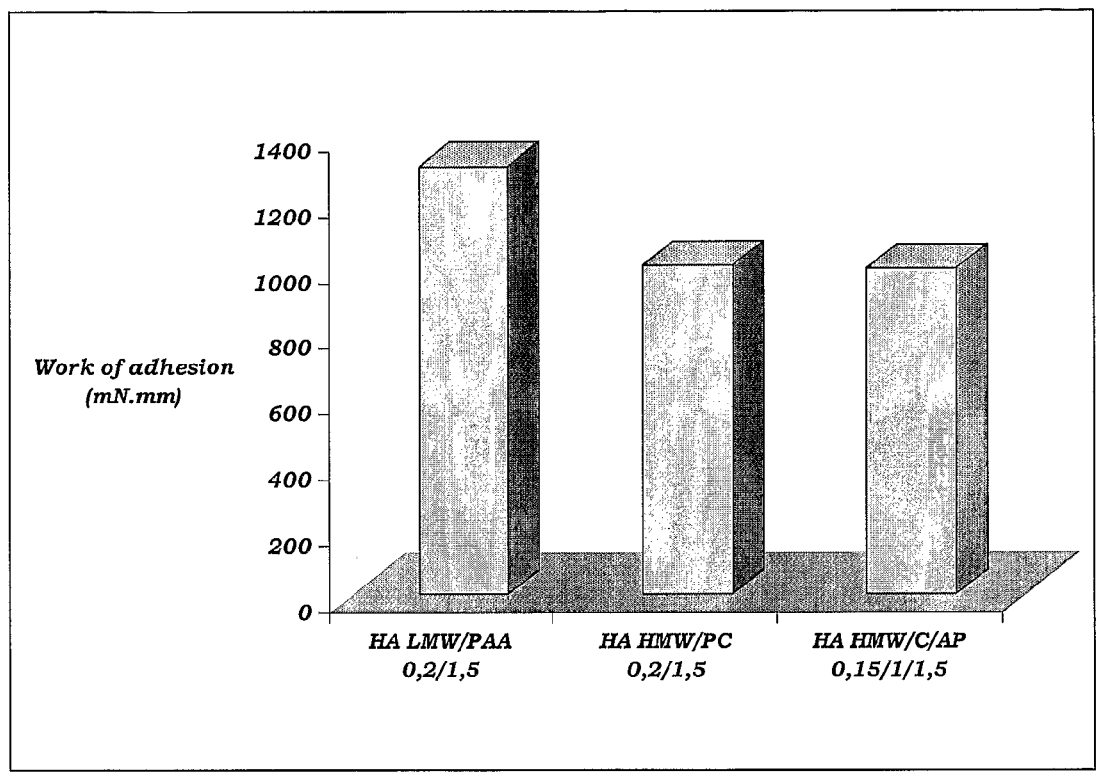
FIG. 5 presents the mucoadhesion work values of tested formulations.

As previously described, topical formulations based on HA and synthetic polymers (including FAA) were already known as controlled drug delivery systems. Patent IT1273742 discloses the use of various kinds of synthetic polymers, polycarbophil and polyvinyl alcohol being selected as the preferred polymers, in combination with HA with a high molecular weight of $1\times10^6$ Da. To demonstrate that the formulations of the invention are better than known compositions, direct comparisons were conducted between formulation 4 (which presents the best performance in terms of mucoadhesion, washability, release and permeation) and two control formulations similar to formulation 4 but with the replacements described above relating to polycarbophil, the molecular weight of HA, and polyvinyl alcohol. FIG. 5 shows the results obtained by comparing the mucoadhesion work of composition 4 with control formulations 1 and 2, demonstrating its clear superiority in terms of mucoadhesion to the skin/mucosa.

Release Test

Figure 3:
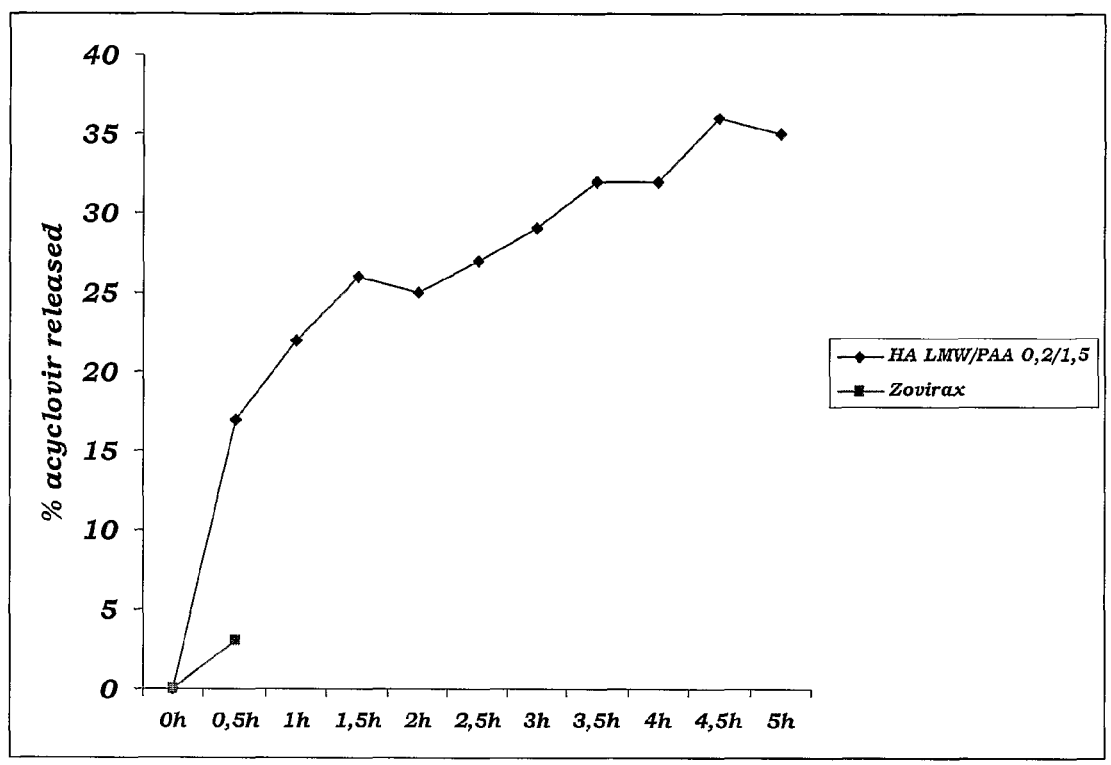
FIG. 3 presents mean acyclovir release profiles for tested formulations.

FIG. 3 shows the mean acyclovir release profiles, obtained in acetate buffer pH 5.0, for formulation 4 and the commercial formulation. It is evident that formulation 4 presents a release profile over time far superior to that of commercial formulation Zovirax®.

"Washability" Test

Figure 4:
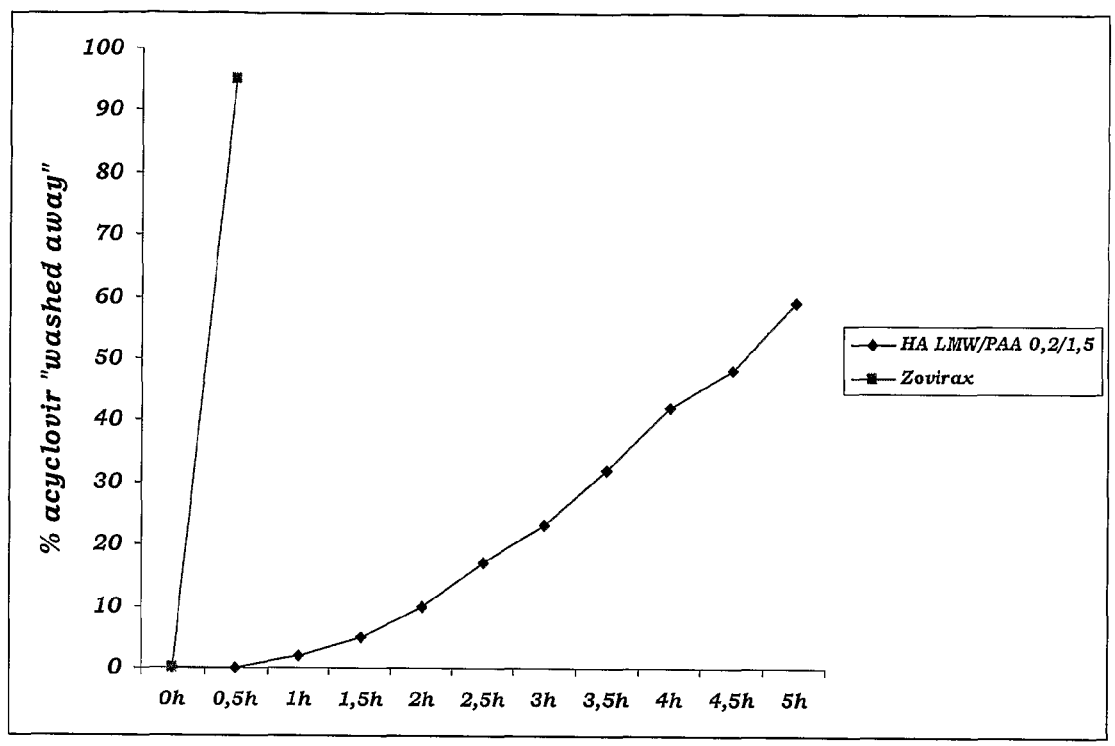
FIG. 4 presents mean profiles of the acyclovir "washed away" by testing formulations.

FIG. 4 shows the mean profiles of the acyclovir "washed away" by the formulations tested. Formulation 4 only reaches the value of 90% of drug "washed away" after 5.5 hours, whereas the commercial formulation is totally removed from the mucosa in the first hour after application.

Conclusions

The tests conducted clearly demonstrate that the association between low molecular weight hyaluronic acid and Carbopol 974P leads to the formation of highly hydrophilic gels which present the best performances in both the mucoadhesion test and the test of washability, permeation and release of active ingredient, not only compared with the commercial cream formulation Zovirax®, but also compared with formulations containing high molecular weight HA and formulations based on PAA without HA.

These properties are considered an invaluable index of stability of the drug acyclovir suspended in said new formulations: in fact, only the strong inner structure of the gel of the invention prevents sedimentation of the active ingredient.

Formulation 4 presents the best performance in terms of mucoadhesion, washability, release and permeation, demonstrating that its ratio between HA concentration (0.2%) and Carbopol concentration (1.5%) is the best among those chosen. The formulation, due to its composition, is consequently able to prolong the release of the drug to the damaged skin/mucosa and to ensure that a larger amount of active ingredient is absorbed. The improved mucoadhesion also allows a lower frequency of administration compared with the cream formulation, with evident advantages of practicality and economy of treatment.

The therapeutic efficacy of the formulations described above proved particularly advantageous due to the action of hyaluronic acid, which also facilitates healing of the ulcers created locally by viruses by keeping the damaged skin and mucous membranes highly hydrated. The new formulations therefore provide both therapeutic efficacy and the best reconstruction properties for the altered dermis and/or mucosa.

The invention claimed is:

1. A topical formulation in the form of a hydrophilic bioadhesive gel comprising (a) acyclovir as an active ingredient in a percentage by weight of between 1 and 10%, (b) low molecular weight sodium hyaluronate comprised of hyaluronic acid (HA) with a molecular weight of between 90,000 and 230,000 Da in a percentage by weight of between 0.1 and 1%, and (c) the acrylic polymer Carbomer in a percentage by weight of 1.5%, wherein said acrylic polymer is at least one member selected from the group consisting of Carbomer 974P and Carbomer 934P.

2. The formulation according to claim 1, wherein acyclovir is present in a percentage by weight of 5%.

3. The formulation according to claim 1, wherein said sodium hyaluronate is present in a percentage by weight of 0.2%.

4. A method for treating mucocutaneous lesions caused by Herpes Simplex and/or Herpes Zoster comprising administering a formulation according to claim 1.

5. A method for the reconstruction of the dermis and mucous membranes damaged by Herpes Simplex and/or Herpes Zoster comprising administering a formulation according to claim 1.

6. A method for the protracted release of an active ingredient to the skin/mucosa damaged by Herpes Simplex and/or Herpes Zoster comprising administering a formulation according to claim 1.

7. The formulation according to claim 2, wherein said sodium hyaluronate has a molecular weight of 200 kDa and is present in an amount of 0.2% by weight.

* * * * *